(12) United States Patent
Wallace

(10) Patent No.: US 6,193,512 B1
(45) Date of Patent: Feb. 27, 2001

(54) WATER JET TEETH CLEANING APPARATUS

(76) Inventor: Stephen C. Wallace, 1174 Hilltop Rd., Erie, PA (US) 16509

( * ) Notice: Subject to any disclaimer, the term of this patent is extended or adjusted under 35 U.S.C. 154(b) by 0 days.

(21) Appl. No.: 09/557,462

(22) Filed: Apr. 25, 2000

(51) Int. Cl.[7] .................................................. A61G 17/02
(52) U.S. Cl. ............................ 433/80; 601/161; 601/162
(58) Field of Search ........................... 433/80, 215, 216; 601/161, 162

(56) References Cited

U.S. PATENT DOCUMENTS

| | | |
|---|---|---|
| 4,638,520 | 1/1987 | Eickmann . |
| 4,673,307 | 6/1987 | Prestele et al. . |
| 4,793,331 | 12/1988 | Stewart . |
| 4,841,590 | 6/1989 | Terry et al. . |
| 5,027,798 | 7/1991 | Primiano . |
| 5,153,962 | 10/1992 | Ritter . |
| 5,218,956 * | 6/1993 | Handler et al. .................... 433/80 X |
| 5,241,714 | 9/1993 | Barry . |
| 5,338,124 | 8/1994 | Spicer et al. . |
| 5,484,281 | 1/1996 | Renow et al. . |
| 5,683,192 | 11/1997 | Kilfoil . |
| 5,746,595 | 5/1998 | Ford . |

\* cited by examiner

Primary Examiner—Nicholas D. Lucchesi
(74) Attorney, Agent, or Firm—Dale J. Ream

(57) ABSTRACT

A jet water teeth cleaning apparatus comprises a shower head for releasably attaching the apparatus to the inlet pipe of a shower. A valve coupled to the shower head selectably diverts water through a flexible tube to a handheld unit. The hand unit includes a housing with a nozzle and a pistol-grip style handle. The handle includes a trigger for regulating the velocity of water allowed to flow through the housing and for actuating a battery powered vibration unit. The vibration unit includes a reciprocating piston which maintains optimal water pressure by stirring the water flow to reduce friction between the water and the channel. The housing further includes a refillable reservoir of dentifrice which communicates a quantity of dentifrice into the water stream channel according to a siphoning or Venturi effect. The water stream with dentifrice is expelled through the nozzle for cleaning or flossing a user's teeth while showering.

20 Claims, 4 Drawing Sheets

Section
4-4

WATER JET TEETH CLEANING APPARATUS

BACKGROUND OF THE INVENTION

This invention generally relates to dental hygiene devices and, more particularly, to a water jet teeth cleaning apparatus which delivers a dentifrice within a high velocity stream of water for cleaning the teeth and gums of a person while showering.

Several devices have been proposed in the prior art which divert water from a shower head or inlet pipe to a brush or flossing tool. Although assumably effective in operation, existing devices still exhibit several disadvantages. Specifically, some devices include complicated apparatus for introducing dentifrice into the water stream. Further, the pressure of the ultimately expelled water stream is often too low to effectively clean a user's teeth. In addition, previous devices do not provide a variable speed control of the water stream that is easy and convenient to operate.

Accordingly, it is desirable to have a teeth cleaning apparatus which can introduce dentifrice into the water stream without external apparatus. It is also desirable to have an apparatus which reduces or even eliminates factors which naturally reduce water pressure. Further, an apparatus having a variable velocity water stream that is simple to operate is needed.

SUMMARY OF THE INVENTION

In response thereto, I have invented a water jet teeth cleaning apparatus which utilizes a shower head releasably attached to the inlet pipe of a shower and having a valve stem for selectably diverting water into a flexible tube. The tube is coupled to a channel within a handheld teeth cleaning unit having a housing with a nozzle and a pistol-grip type handle assembly. The handle assembly includes a trigger for regulating the volume of water allowed to flow through the housing. Depression of the trigger allows water to flow through the housing and also actuates a vibration device which stirs the water stream to discourage frictional bonding so as to maintain optimal water pressure. The housing further includes a refillable reservoir of dentifrice which introduces the dentifrice into the water stream channel through a siphoning or Venturi effect. The water stream with dentifrice mixed therein is then forcefully expelled from an arcuate tip of the nozzle for cleaning or flossing the teeth of a person while showering.

It is therefore a general object of the invention to provide a teeth cleaning apparatus which can be attached to the inlet pipe of a shower so as to use the water stream directed thereto.

A further object of the invention is to provide a teeth cleaning apparatus, as aforesaid, having a pistol grip type handle which is easy to hold by a person while showering.

Another object of the invention is to provide a teeth cleaning apparatus, as aforesaid, in which the velocity of the water stream flowing therethrough can be regulated from the shower head or from a trigger assembly on the handle.

Still another object of the invention is to provide a teeth cleaning apparatus, as aforesaid, having a reservoir within the apparatus housing which introduces dentifrice into a water stream through a siphon or Venturi effect.

Yet another object of the invention is to provide a teeth cleaning apparatus, as aforesaid, having a vibration device which inhibits decreased fluid velocity caused by frictional forces.

A further object of the invention is to provide a teeth cleaning apparatus, as aforesaid, which is compact, self-contained, and easy to attach or remove from a shower inlet pipe.

Other objects and advantages of the invention will become apparent from the following description taken in connection with the accompanying drawings, wherein is set forth by way of illustration and example, an embodiment of the invention.

DESCRIPTION OF THE PREFERRED EMBODIMENT

A water jet teeth cleaning apparatus 10 according to a preferred embodiment of the present invention will now be described with reference to FIGS. 1–4.

Figures 1A, 1B:
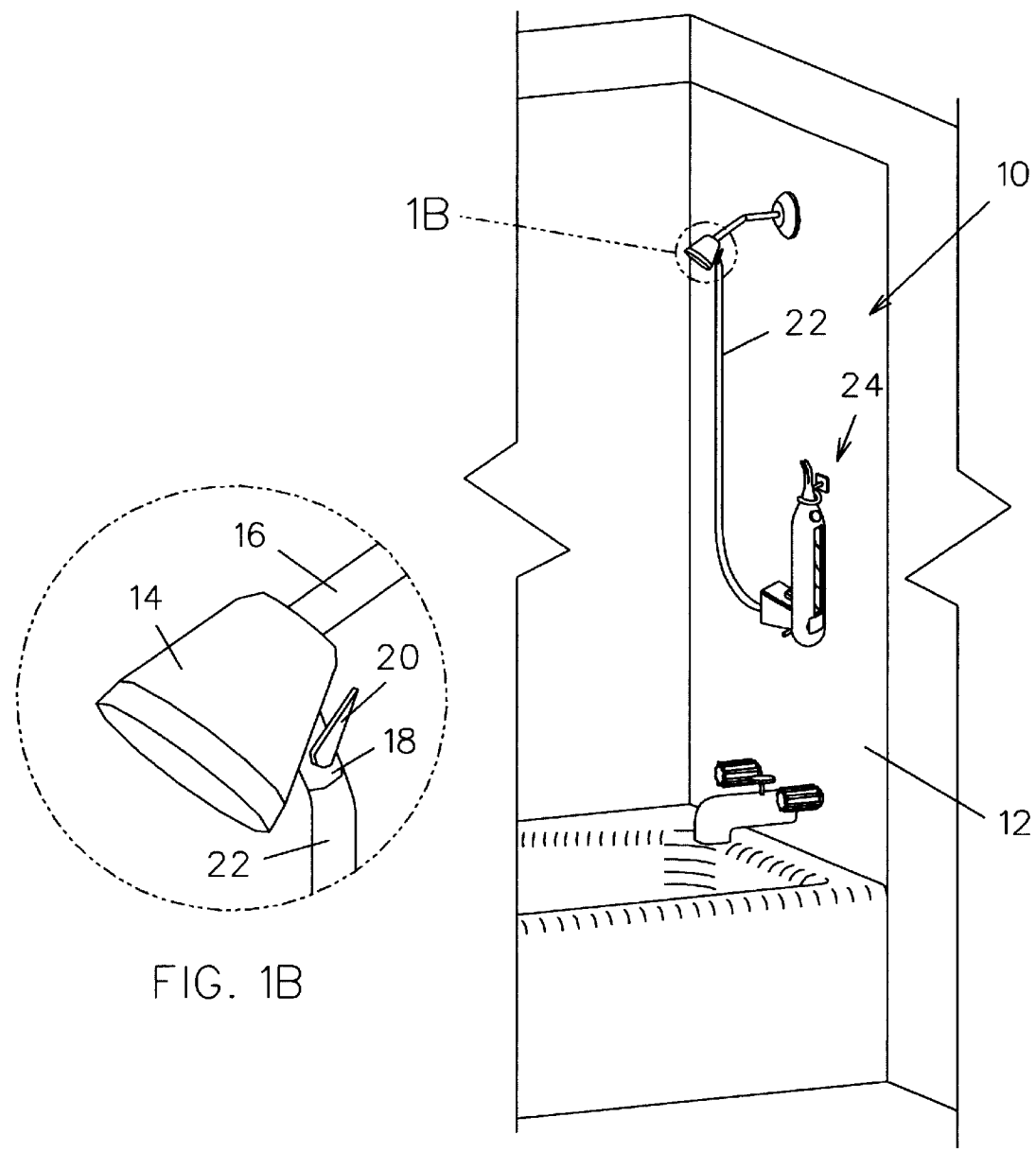
FIG. 1A is a perspective view of the preferred embodiment of the teeth cleaning apparatus installed in a conventional shower.
FIG. 1B is an isolated perspective view on an enlarged scale of the valve stem of the shower head.

FIG. 1 shows a shower head 14 threadably coupled to the inlet water pipe 16 of a conventional shower 12 such that the entire apparatus can be quickly and easily installed or removed from a shower. One end of a flexible tube 22 is attached to a valve stem 18 of the shower head 14 which diverts water therefrom with an opposed end of the tube being fixedly attached to a handheld teeth cleaning unit 24. Valve stem 18 includes a lever 20 (FIG. 1B) which allows a user to manually regulate the flow of water from the inlet pipe 16 to the hand unit 24.

Figure 2:
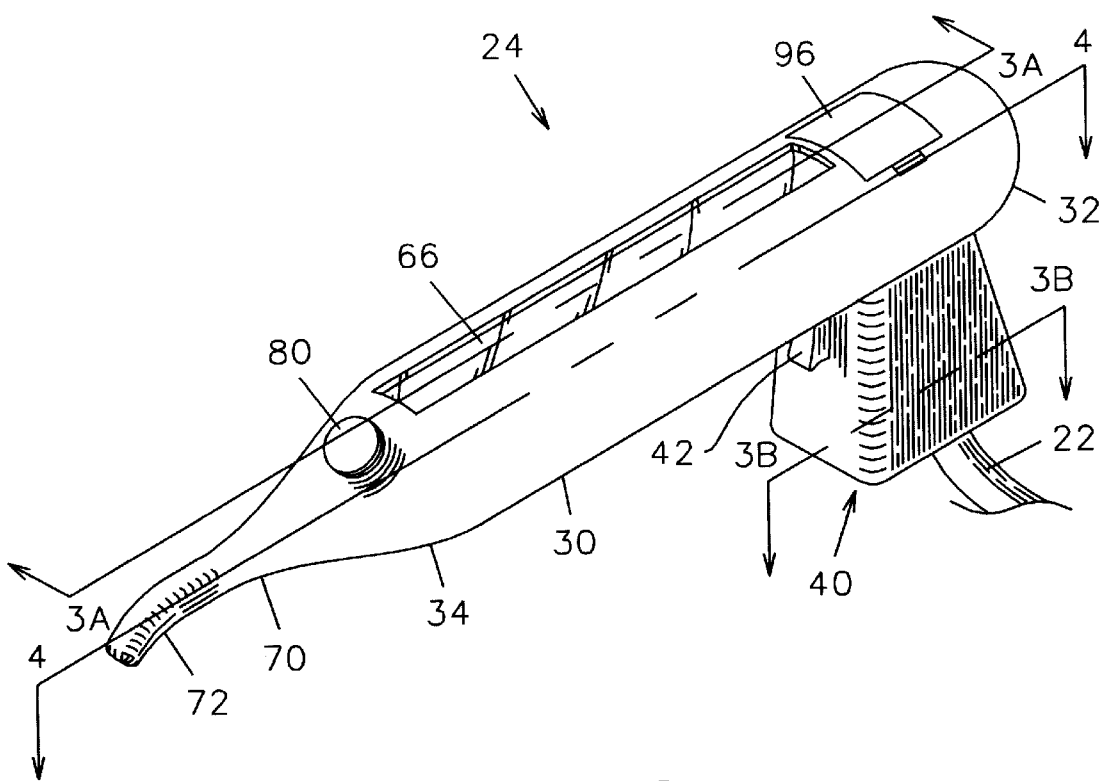
FIG. 2 is a perspective view of the teeth cleaning apparatus of FIG. 1 removed from the shower.
Figures 3A, 3B:
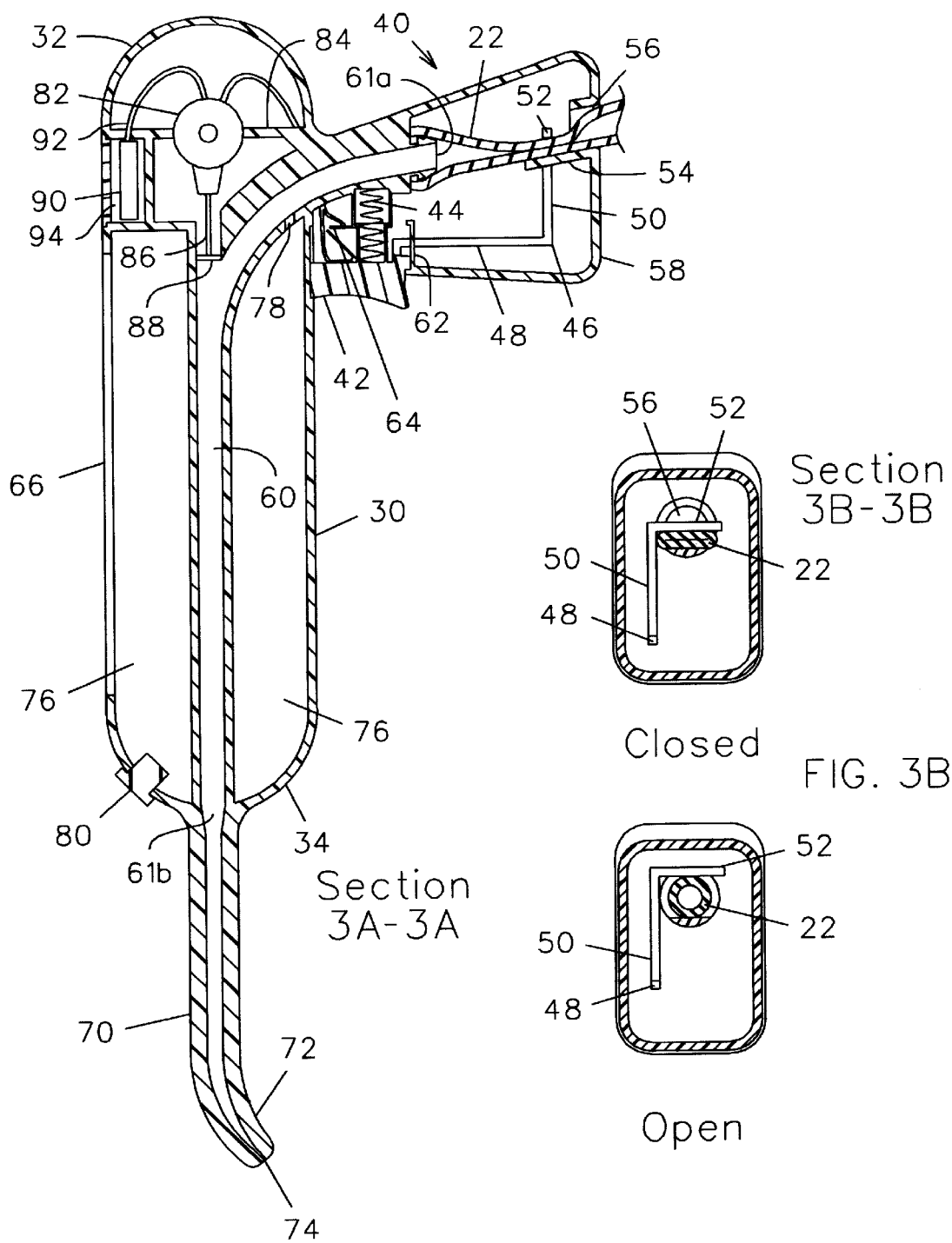
FIG. 3A is a sectional view of the teeth cleaning apparatus taken along line 3A—3A of FIG. 2.
FIG. 3B is a sectional view of the handle assembly of the apparatus taken along line 3B—3B of FIG. 2 showing the water stream tube in a first closed position and a second open position.
Figure 4:
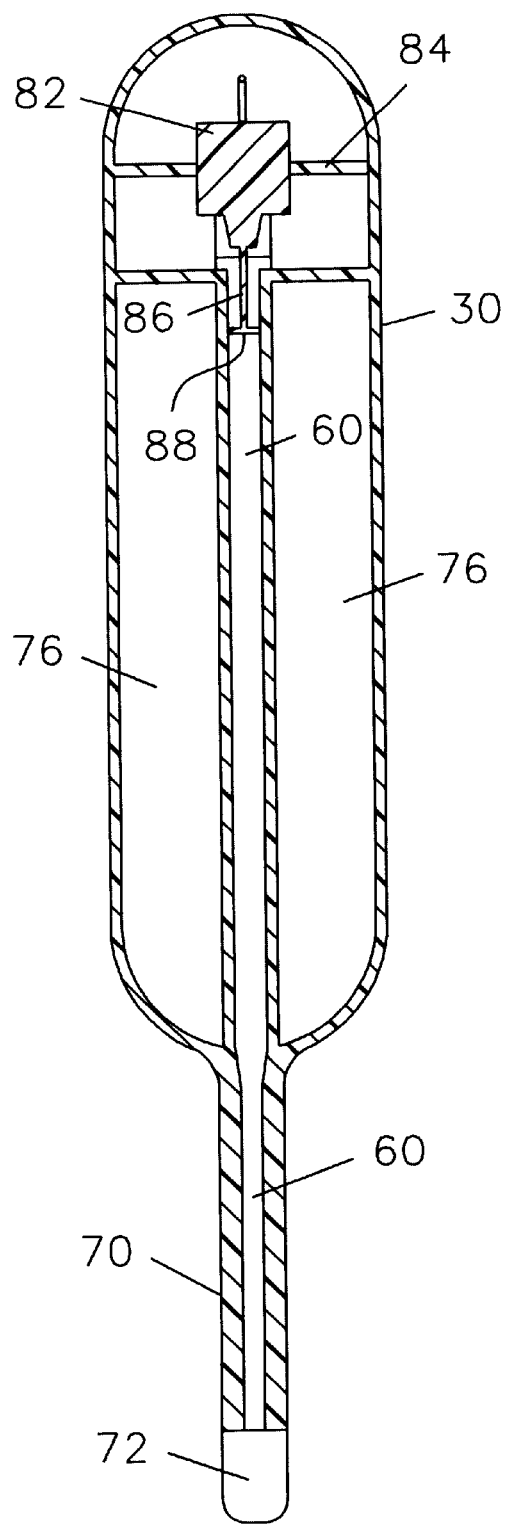
FIG. 4 is a sectional view of the apparatus taken along line 4—4 of FIG. 2.

As better shown in FIGS. 2 and 3A, the handheld teeth cleaning unit 24 comprises an elongated hollow cylindrical housing 30 having upstream and downstream ends 32, 34 and a hollow pistol-grip type handle 40 fixedly attached to the housing 30 near the upstream end 32. The flexible tube 22 extends through an inlet aperture 56 defined by the bottom wall 58 of the handle 40 and is fixedly coupled to an inlet port 61a of a tubular channel 60. The channel 60 extends through the housing 30 and further defines an outlet 61b port. The channel is preferably constructed from a more rigid material such as plastic conduit. The handle 40 includes a trigger 42 having an interior edge. A spring 44 is positioned between the interior edge of the trigger 42 and the channel 60. During use, the spring 44 is compressed when the trigger 42 is depressed by a user so as to resiliently restore the trigger 42 to its non-depressed position upon release. A brake arm 62 is also mounted within the handle 40 and positioned relative to the trigger 42 so as to prevent a potentially damaging over-depression of the trigger 42.

A clamping member 46 is attached to the interior edge of the trigger 42 within the housing 30. The clamping member 46 comprises a first downwardly extending arm 48 having one end fixedly attached to the interior edge of the trigger 42 and an opposed end normal to a second arm 50. The second arm 50 extends to a point adjacent the water stream tube 22. A flange 52 normal to the free end of the second arm 50 engages one side of the tube 22 for selectably and incrementally clamping the tube 22 against a post 54, as to be described more fully below.

The channel 60 extends upwardly from within the handle 40 into the interior space of the housing 30 and extends therefrom along the longitudinal axis of the housing 30. The channel 60 further extends into a nozzle 70 integrally attached to the downstream end 34 of the housing 30, the nozzle having an arcuate tip 72. The channel portion within the housing 30 is completely surrounded by a reservoir 76 for holding a quantity of dentifrice. A wall of the channel 60 defines a slot 78 which allows dentifrice to be drawn from the reservoir into the water stream of the channel 60. More particularly, dentifrice is siphoned from the reservoir 76 through the slot 78 and into the channel 60 according to the Venturi effect, the rate of dentifrice withdrawal depending upon the size of the slot 78 and the velocity of the water passing thereover.

One side of the housing 30 includes an elongated window 66 such that a user can monitor the quantity of dentifrice remaining within the reservoir 76. The wall of the housing 30 also defines an aperture through which additional dentifrice can be added to the reservoir by removing a plug 80 or stopper therefrom and depositing dentifrice therein.

An electromechanical vibration device 82 is fixedly mounted to a strut 84 within the upstream end 32 of the housing 30. The vibrator 82 is coupled to a battery power source 90 with a wire 92 (FIG. 3A). The battery 90 rests within a compartment 94 of the housing 30 and may be accessed through an access door 96 frictionally fitted thereto. The vibrator 82 is actuated as the trigger 42 is depressed causing a lead 64 to be joined to close a circuit. The vibrator 82 includes a piston 86 having a circular flange 88 integrally attached to a free end thereof which extends into the water stream channel 60 of the housing 30 and reciprocates therein at a high frequency. Mechanical vibrations introduced into the channel 60 stir the flow of water to reduce VanDerWaals or molecular bonding of the water molecules. Thus, friction of the water stream against the channel walls is reduced so as to promote optimum water pressure.

In operation, the apparatus 10 is attached to the inlet pipe 16 of a shower 12 by threadably coupling the shower head 14 thereto. Water is passed through the shower head in the conventional manner so long as the valve stem 18 is in its closed position. Conversely, water is diverted to the apparatus when the valve 18 is open. The valve 18 is selectably opened or closed by pivoting the lever 20. Water flowing through the water stream tube 22 is again regulated within the handle 40 of the hand unit 24. When the trigger 42 is in its non-depressed or released position, the walls of the tube 22 are tightly clamped against the post 54 by the clamping assembly 46 (FIG. 3B). Depression of the trigger 42, however, incrementally and rearwardly extends the clamping assembly 46 so as to release the compression of the tube 22 and allow the water stream to flow therethrough. Upon release of the trigger 42, the tube is again constricted as the trigger is urged to its non-depressed position by the resilient action of the compression spring 44. It is understood that the trigger 42 may be variably positioned by the user to regulate the volume and thus the velocity of the water stream.

As the trigger 42 is pressed and water is allowed to flow through the channel 60 within the housing 30, the vibration unit 82 is activated to stir the flow, prevent friction and molecular bonding, and thus maintain optimal water pressure. As the water stream flows over the slot 78 between the reservoir 76 and channel 60, dentifrice is drawn from the reservoir into the channel 60 according to the Venturi effect whereby an increased velocity of the water stream correspondingly decreases the pressure exerted against the dentifrice at the slot opening, thus drawing dentifrice into the channel 60. The jet water stream now containing dentifrice is then expelled from the housing through a narrow opening 74 in the tip 72 of the nozzle 70. It will be appreciated that as the channel 60 narrows toward the opening 74, the velocity of the water stream increases.

Accordingly, the jet water teeth cleaning apparatus 10 can provide inline addition of dentifrice to a water stream while optimizing the velocity of water flow therethrough. Further, the apparatus 10 provides a convenient handle grip 40 with a trigger 42 for further regulating water velocity.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A handheld water jet teeth cleaning apparatus for attachment to a conventional shower head, comprising:

a housing defining an interior space and having a channel extending therethrough between opposed upstream and downstream ends, said channel defining inlet and outlet ports;

means for coupling said inlet port of said channel to the showerhead, whereby water flowing through the shower head is selectably communicated through said inlet port into said channel;

a battery power source mounted within said interior space of said housing; and a vibration device mounted within said interior space of said housing and electrically coupled to said power source, said vibration device having a piston member in communication with said channel and adapted to selectably reciprocate at a high frequency so as to inhibit frictional bonding of water molecules flowing through said channel.

2. A teeth cleaning apparatus as in claim 1 wherein said coupling means includes:

a valve coupled to the shower head adapted to selectably divert water therefrom; and a flexible tube having a first end coupled to said inlet port of said channel and a second end coupled to said valve for selectably diverting water from the showerhead to said channel.

3. A teeth cleaning apparatus as in claim 2 further comprising:

a trigger coupled to said housing and incrementally movable between a released position and a depressed position; and a clamping member coupled to said trigger and adapted to fully constrict said tube when said trigger is at said released position so as to preclude a fluid flow through said tube and to fully release said tube when said trigger is at said depressed position so as to enable a fluid flow therethrough.

4. A teeth cleaning apparatus as in claim 3 wherein said trigger presents an interior edge;

said teeth cleaning apparatus further comprising a spring positioned between said interior edge of said trigger and said channel, whereby said spring is compressed upon movement of said trigger to said depressed position.

5. A teeth cleaning apparatus as in claim 3 wherein said clamping member further includes:

a first arm having one end attached to said trigger and an opposed end; and a second arm having a first end normal to said opposed end of said first arm and a second end configured so to constrict said tube when said trigger is at said released position and to release said tube when said trigger is at said depressed position.

6. A teeth cleaning apparatus as in claim 3 wherein said trigger is electrically connected to said power source so as to actuate said vibration device when said trigger is at said depressed position;

said piston includes a circular flange attached to a free end thereof extending into said channel so as to stir the water therein as said piston reciprocates.

7. A teeth cleaning apparatus as in claim 2 wherein said housing further includes a handle having a bottom wall defining an inlet aperture for receiving said first end of said flexible tube therethrough, said handle having a break arm positioned therein for preventing over-depression of said trigger.

8. A teeth cleaning apparatus as in claim 1 wherein said housing further includes a reservoir mounted within said interior space for receiving dentifrice therein, said housing defining a window adapted to allow a user to view the quantity of dentifrice contained within said reservoir.

9. A teeth cleaning apparatus as in claim 1 wherein said housing further includes a nozzle attached to said downstream end thereof in communication with said outlet port of said channel.

10. A hand-held teeth cleaning apparatus for attachment to a conventional shower head, comprising:

a housing defining an interior space and having a channel extending therethrough between opposed upstream and downstream ends, said channel defining inlet and outlet ports;

a flexible tube having first and second ends, said first end coupled to said inlet port of said channel;

means for connecting said second end of said tube to the showerhead, whereby water flowing through the shower head is diverted from the shower head through said inlet port into said channel;

a trigger coupled to said housing and incrementally movable between a released position and a depressed position; and a clamping member having a first end coupled to an interior edge of said trigger and a second end adapted to constrict said tube when said trigger is at said released position so as to preclude a fluid flow through said tube and to release said tube when said trigger is at said depressed position so as to enable a fluid flow therethrough.

11. A teeth cleaning member as in claim 10 further including:

a battery power source mounted within said interior space of said housing;

a vibration device mounted within said interior space of said housing and electrically coupled to said power source, said vibration device having a piston member in communication with said channel and adapted to selectably reciprocate at a high frequency so as to inhibit bonding of water molecules flowing through said channel; and said trigger electrically connected to said power source and adapted to actuate said vibration device when said trigger is at said depressed position.

12. A teeth cleaning apparatus as in claim 11 wherein said piston member includes a circular flange attached to a free end thereof for stirring water within said channel as said piston reciprocates.

13. A teeth cleaning apparatus as in claim 10 wherein said trigger presents an interior edge;

said teeth cleaning apparatus further comprising a spring positioned between said interior edge of said trigger and said channel, whereby said spring is compressed upon movement of said trigger to said depressed position.

14. A teeth cleaning apparatus as in claim 10 wherein said housing further includes a handle defining an interior space in communication with said interior space of said housing, said inlet port of said channel extending within said interior space of said handle, said handle having a bottom wall defining an aperture for receiving said first end of said flexible tube therethrough.

15. A teeth cleaning apparatus as in claim 10 wherein said housing further includes a reservoir mounted within said interior space for receiving dentifrice therein, said housing defining a window for viewing the quantity of dentifrice contained within said reservoir.

16. A teeth cleaning apparatus as in claim 10 wherein said housing further includes a nozzle attached to said downstream end thereof in communication with said outlet port of said channel.

17. A teeth cleaning apparatus, comprising:

a housing defining an interior space and having a channel extending therethrough between opposed upstream and downstream ends, said channel defining inlet and outlet ports;

a valve coupled to a conventional shower head adapted to selectably divert water therefrom; and a flexible tube having a first end coupled to said inlet port of said channel and a second end coupled to said valve for selectably diverting water from said showerhead to said channel;

a reservoir mounted within said interior space for receiving dentifrice therein, said housing having a window adapted to allow a user to view the quantity of dentifrice contained within said reservoir;

a battery power source mounted within said interior space of said housing; and a vibration device mounted within said interior space of said housing and electrically coupled to said power source, said vibration device having a piston member in communication with said channel and adapted to selectably reciprocate at a high frequency so as to inhibit bonding of water molecules flowing through said channel.

18. A teeth cleaning device as in claim 17 further comprising:

a trigger coupled to said housing and movable between a released position and a depressed position; and a clamping member coupled to said trigger and adapted to constrict said tube when said trigger is at said released position so as to preclude a fluid flow through said tube and to release said tube when said trigger is at said depressed position so as to enable a fluid flow therethrough.

19. A teeth cleaning apparatus as in claim 17 wherein said housing further includes a handle having a bottom wall defining an inlet aperture for receiving said first end of said flexible tube therethrough.

20. A teeth cleaning apparatus as in claim 17 wherein said trigger is electrically connected to said power source so as to actuate said vibration device when said trigger is at said depressed position;

said piston includes a circular flange attached to a free end thereof extending into said channel so as to stir the water therein as said piston reciprocates.

* * * * *